US008513214B2

(12) United States Patent
Vu et al.

(10) Patent No.: US 8,513,214 B2
(45) Date of Patent: Aug. 20, 2013

(54) C4'-SUBSTITUTED-2-DEOXYADENOSINE ANALOGS AND METHODS OF TREATING HIV

(75) Inventors: Bao-Han C. Vu, Frederick, MD (US); Maqbool A. Siddiqui, Silver Spring, MD (US); Victor E. Marquez, Montgomery Village, MD (US); Stephen H. Hughes, Smithsburg, MD (US); Paul L. Boyer, Greencastle, PA (US)

(73) Assignee: The United States of America as Represented by the Secretary of the Dept. of Health and Human Services, Washington, DC (US)

( * ) Notice: Subject to any disclaimer, the term of this patent is extended or adjusted under 35 U.S.C. 154(b) by 155 days.

(21) Appl. No.: 12/741,873

(22) PCT Filed: Nov. 10, 2008

(86) PCT No.: PCT/US2008/012663
§ 371 (c)(1), (2), (4) Date: Aug. 24, 2010

(87) PCT Pub. No.: WO2009/064387
PCT Pub. Date: May 22, 2009

(65) Prior Publication Data
US 2011/0190226 A1 Aug. 4, 2011

Related U.S. Application Data

(60) Provisional application No. 61/002,711, filed on Nov. 9, 2007.

(51) Int. Cl.
| | | |
|---|---|---|
| A01N 43/04 | (2006.01) | |
| A61K 31/70 | (2006.01) | |
| C07H 19/16 | (2006.01) | |
| C07H 19/167 | (2006.01) | |
| C07H 19/173 | (2006.01) | |
| C12Q 1/70 | (2006.01) | |

(52) U.S. Cl.
USPC ............... 514/45; 514/46; 435/5; 536/27.21; 536/27.6

(58) Field of Classification Search
None
See application file for complete search history.

(56) References Cited

PUBLICATIONS

Shuto et al., Journal of Organic Chemistry (1997), 62(17), 5676-5677.*
Kendrick et al., Chemical Communications (2002) vol. 18, pp. 2016-2017.*
Freireich et al., "Quantitative Comparison of Toxicity of Anticancer Agents in Mouse, Rat, Hamster, Dog, Monkey, and Man", Cancer Chemotherapy Reports, May 1966; 50(4): 219-244.
Julias et al., "Replication of Phenotypically Mixed Human Immunodeficiency Virus Type 1 Virions Containing Catalytically Active and Catalytically Inactive Reverse Transcriptase", J. Virol., Jul. 2001; 75(14): 6537-6546 Abstract Only (15 pages).
Boyer P L et al: "The Nucleoside Analogs 4'C-Methyl Thymidine and 4'C-Ethyl Thymidine Block DNA Synthesis by Wild-type HIV-1 RT and Excision Proficient NRTI Resistant RT Variants", Journal of Molecular Biology, Academic Press, United Kingdom, vol. 371, No. 4, Aug. 24, 2007, pp. 873-882.
Hayakawa H et al: "Potential of 4'-C-substituted nucelosides for the treatment of HIV-1" Antiviral Chemistry & Chemotherapy, Blackwell Scientific Publ., London, GB, vol. 15, No. 4, Jul. 1, 2004, pp. 169-187.
Ohrui Hiroshi: "2'-deoxy-4'-C-ethynyl-2-fluoroadenosine, a nucleoside reverse transcriptase inhibitor, is highly potent against all human immunodeficiency viruses type 1 and has low toxicity.", Chemical Record (New York, N.Y.), vol. 6, No. 3, 2006, pp. 133-143.
International Search Report; International Application No. PCT/US2008/012663; International Filing Date Nov. 10, 2008; 7 pages.
Ohrui et al: "4'-C-Substituted-2'-Deoxynucleosides A Family of Antiretroviral Agents Which are Potent Against Drug-Resistant HIV Variants", Current Drug Targets. Infectious Disorders, Bentham Science Publishers, Hilversum, NL, vol. 1, No. 1, May 1, 2001, pp. 1-10.
Rangam G et al: "Synthesis and application of 4'-C-alkylated uridines as probes for uracil-DNA glycosylase", Synthesis, No. 9, Jun. 6, 2005, pp. 1467-1472.
Waga T et al: "Synthesis and Biological Evaluation of 4'-C-Methyl Nucleosides", Nucleosides & Nucleotides, Marcel Dekker, Inc, US, vol. 15, No. 1-03, Jan. 1, 1996, pp. 287-304.
Written Opinion of the International Searching Authority; International Application No. PCT/US2008/012663; International Filing Date Nov. 10, 2008; 18 pages.

* cited by examiner

*Primary Examiner* — Traviss C McIntosh, III
(74) *Attorney, Agent, or Firm* — Cantor Colburn LLP

(57) ABSTRACT

The invention provides for novel 2-Deoxyadenosine compounds, which can treat HIV infection at low cytotoxicity values. Substitution at the 4'-position provided compounds which demonstrated low cytotoxicity values in an ATP-based cytotoxicity assay.

17 Claims, 9 Drawing Sheets

◇C4'Me-2-dA: $EC_{50}$ 48 nM
◇C4'Et-2-dA: $EC_{50}$ 358 nM

Inhibitory effect against AZT-R, SSGR+215, and Q151M Complex, but not M184V

Relative infectivity of HIV-1 in cells pretreated with either
C4'-methyl-2-deoxyadenosine or C4'-ethyl-2-deoxyadenosine compounds

| Compound Cell Line | EC$_{50}$ (nM) | CC$_{50}$ (μM) | Selective Index |
|---|---|---|---|
| C4'-Methyl-2-deoxyadenosine | | | |
| HOS | 63±7 | 62 | 984 |
| TZM-b1 | 69±4 | 176 | 2550 |
| C4'-Ethyl-2-deoxyadenosine | | | |
| HOS | 221±13 | 363 | 1642 |
| TZM-b1 | 184±20 | 186 | 1011 |

Anti-HIV-1 activities and cellular cytotoxicities of C4'-alkylated - 2-deoxyadenosine compounds in varying cell lines

FIG. 9

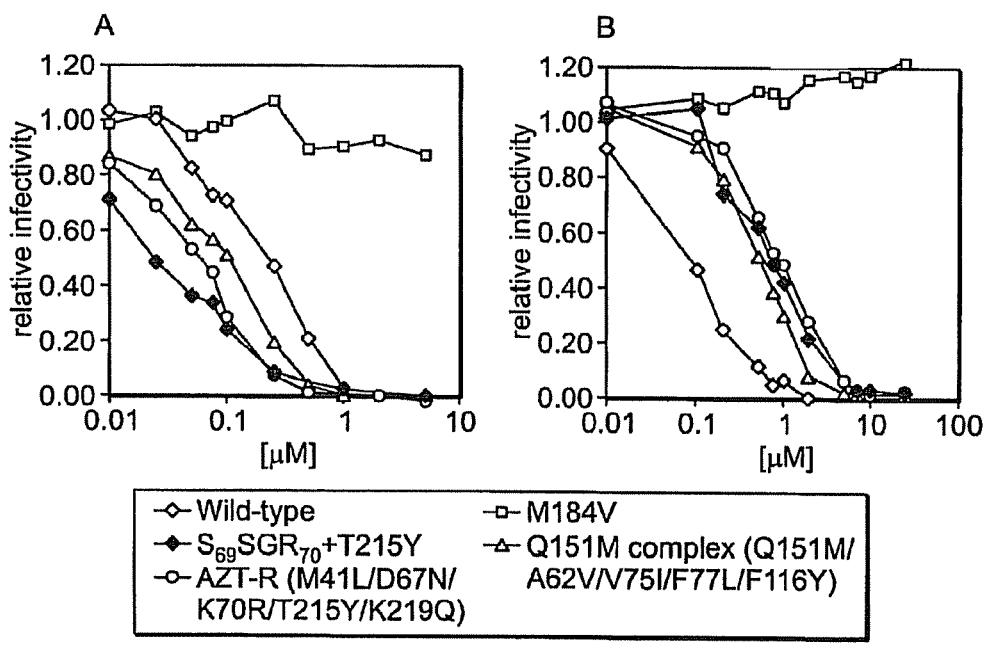

Relative infectivity of HIV-1 carrying NRTI resistance mutations in HOS cells pretreated with either (A) C4'-methyl-2-deoxyadenosine or (B) C4'-ethyl-2-deoxyadenosine

FIG. 10

| Compound | EC$_{50}$ (nM) | Selective Index[a] |
|---|---|---|
| C4'-Methyl-2-deoxyadenosine | | |
| M184V | n.d.[b] | n.d.[b] |
| AZT-R | 64±5 | 969 |
| S$_{69}$SGR$_{70}$+T215Y | 24±9 | 2583 |
| Q151M complex | 111±8 | 559 |
| | | |
| C4'-Ethyl-2-deoxyadenosine | | |
| M184V | n.d.[b] | n.d.[b] |
| AZT-R | 869±65 | 417 |
| S$_{69}$SGR$_{70}$+T215Y | 700±100 | 519 |
| Q151M complex | 519±25 | 699 |

Anti-HIV-1 activities of C4'-alkylated-2-deoxyadenosine compounds in HIV-1 carrying NRTI-resistant reverse transcriptase

[a] Selective Indicies are based on HOS cell cytotoxicities in Table I

[b] The virus carrying the M184V NRTI resistance mutation is resistant against the selected compounds.

FIG. 11

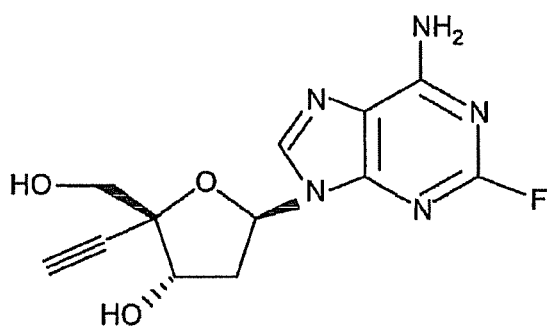

C4'-ethynl-deoxy-2-fluoroadenosine, an NRTI, shown by Mitsuya and co-workers to be effective against the wild-type and the M184V reverse transcriptase variant of HIV-1 MT-4 cells.

FIG. 12

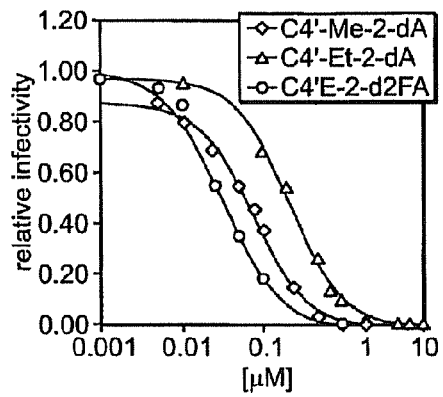

Relative infectivity of HIV-1 in HOS cells pretreated with C4'-ethyl-deoxy-2-fluoroadenosine. The relative infectivity is shown in comparison to the C4'-methyl-2-deoxyadenosine or C4'-ethyl-2-deoxyadenosine compounds, which are the subject of this work

FIG. 13

| Compound | $EC_{50}$ (nM) | $CC_{50}$ (μM) | Selective Index |
|---|---|---|---|
| C4'-Ethynl-2-deoxy-2-fluoro-adenosine | | | |
| WT | 31±2 | 112 | 3613 |
| M184V | 124±5 | - | 903 |

Efficacy and cellular cytotoxicity of C4'-Ethynl-2-deoxy-2-fluoro-adenosine in wind-type and M184V(RT) HIV-1

FIG. 14

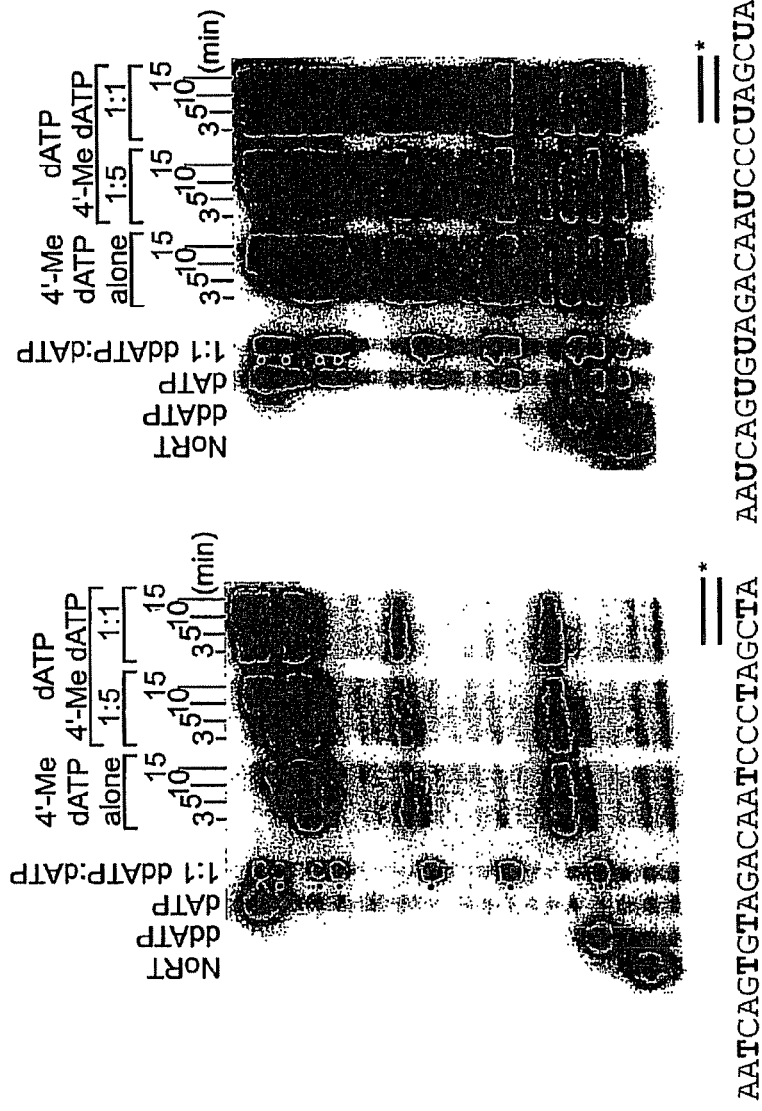

In vitro DNA extension using purified, recombinant HIV-1 RT, with varying amounts of C4'-methyl-2-deoxyadenosinetriphosphate and either (A) a DNA template or (B) and RNA template. Polymerase activity in the presence of dideoxyATP shows expected DNA products resulting from immediate chain terminators, while the dATP lane shows the fully extended DNA products. Bands in the lane containing equimolar amounts of ddATP and dATP correspond to pausing events at the site of incorporation of the nucleosidetriphosphate analog.

US 8,513,214 B2

C4'-SUBSTITUTED-2-DEOXYADENOSINE ANALOGS AND METHODS OF TREATING HIV

CROSS REFERENCE TO RELATED APPLICATIONS

This is a U.S. national stage of application No. PCT/US2008/012663, filed on 10 Nov. 2008. Priority under 35 U.S.C. §119(a) and 35 U.S.C. §365(b) is claimed from U.S. Provisional Patent Application No. 61/002,711, filed 9 Nov. 2007, the disclosure of which is also incorporated herein by reference.

FIELD OF THE INVENTION

The invention provides for novel 2-Deoxyadenosine compounds having low cytotoxicity values, which are useful to treat HIV infection.

BACKGROUND

The human immunodeficiency virus (HIV) and various mutants including type 1 (HIV-1), is the etiological agent of acquired immune deficiency syndrome (AIDS) and related disorders. DNA synthesis during reverse transcriptase is a crucial step in the virus life cycle of human immunodeficiency virus (HIV), and therefore compounds that affect DNA synthesis during the reverse transcriptase process are candidates for antiretroviral therapy. The screening and investigation of novel drugs against HIV remains critical because of the ongoing AIDS epidemics and of the fast emergence of virus variants resistant to present antiviral therapy. The replication steps of HIV, a member of the retrovirus family, are well known and can therefore be targeted rationally.

Substituted-2-deoxyadenosine compounds which are substituted at the C4'-position with variously substituted groups are known, and some have been disclosed as useful in treating viral infection, including HIV. Various 2-Deoxyadenosine compounds have been disclosed having a methyl, ethynyl, halomethyl, halovinyl, or nitrile substitution at the C4' position. These compounds have been shown to be useful against HIV but have been limited to due problematic cytotoxicity ranges.

The instant invention seeks to provide novel substituted-2-deoxyadenosine compounds that are useful to treat HIV, wherein such compounds have reduced cytotoxicity profiles.

BRIEF SUMMARY OF THE INVENTION

In one aspect, the invention provides a compound of Formula (I), or pharmaceutically acceptable salt, solvate or hydrate thereof:

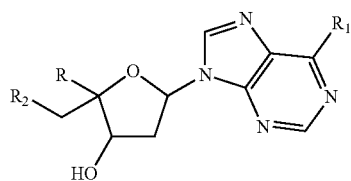

Formula (I)

wherein,
R is $C_1$-$C_{12}$ alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;
$R^1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;
$R_2$ is $NR_aR_b$, $OR_b$, or $S(O)_nR_b$;
$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;
$R_b$, for each occurrence, is independently, H, an optionally substituted $C_{1-6}$alkyl, an optionally substituted $C_{4-12}$aralkyl, wherein,
R is $C_2$-$C_{12}$alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;
$R^1$ is H, $C_1$-$C_{12}$alkyl, $C_3$-$C_{12}$aryl, $C_3$-$C_{12}$heteroaryl, $C_4$-$C_{12}$aralkyl, $C_4$-$C_{12}$heteroalkyl, $NR_aR_b$, or $OR_b$, each of which is optionally substituted;
$R_2$ is $NR_aR_b$, $OR_b$, or $S(O)_nR_b$;
$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;
$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and
n is 0-2.

In another aspect the invention provides for a pharmaceutical composition comprising one or more compounds of Formula (I) and a pharmaceutically acceptable carrier.

In another aspect, the invention provides a kit comprising an effective amount of one or more compounds of Formula (I) in unit dosage form, together with instructions for administering the compound to a subject suffering from or susceptible to a viral infection.

In one aspect, the invention provides for a method of treating a subject suffering from or susceptible to a viral infection comprising administering to the subject an effective amount of one or more compounds of formula (I).

In another aspect, the invention provides a method of treating a subject suffering from or susceptible to HIV infection comprising administering to the subject an effective amount of one or more compounds of formula (I).

In certain aspects, the invention provides a method of treating a subject suffering from or susceptible to HIV infection comprising administering to the subject an effective amount of one or more compounds of formula (I):

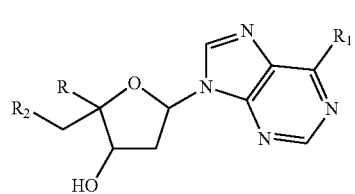

Formula (I)

an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the administered compound has a $CC_{50}$ of greater than 50 μM in a cytotoxicity assay comprising the following steps:

a) contacting cells with the compound of formula I; and b) determination of relative cytotoxicity using a detection kit;

wherein the detection kit comprises a luciferase reporter system and cellular ATP.

In another aspect, the invention provides a method for identifying a compound of formula (I) which blocks viral infectivity,

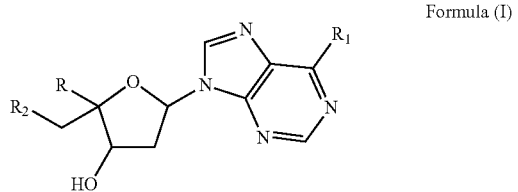

Formula (I)

wherein,

R is $C_1$-$C_{12}$ alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;

$R^1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the compound has a $CC_{50}$ of greater than 50 μM;

the method comprising the following steps:

a) contacting cells with the compound of formula I;

b) detecting a decrease of viral infection; and c) determining an amount of decrease of viral infection.

DESCRIPTION OF THE DRAWINGS

FIG. 3 shows that the target compounds were not cytotoxic in the effective treatment range, with $CC_{50}$ values in excess of 50 μM. The $CC_{50}$ to $EC_{50}$ ratio was used in therapeutic development as the selectivity index. Higher SIs indicate that the compounds of the invention would not interfere with effective treatment owing to low cytotoxicity. The data shows that the SIs for the compounds of the invention is high, greater than 500 for C4'Me-2-dA and greater than 140 for C4'Et-2-dA.

FIG. 9. Anti-HIV-1 activities and cellular cytotoxicities of C4'-alkylated-2-deoxyadenosine compounds in varying cell lines.

FIG. 10. Relative infectivity of HIV-1 carrying NRTI resistance mutations in HOS cells pretreated with either (A) C4'-methyl-2-deoxyadenosine or (B) C4'-ethyl-2-deoxyadenosine.

FIG. 11. Anti-HIV-1 activities of C4'-alkylated-2-deoxyadenosine compounds in HIV-1 carrying NRTI-resistant reverse transcriptase;

FIG. 12. C4'-ethynl-deoxy-2-fluoroadenosine, an NRTI, shown by Mitsuya and co-workers to be effective against the wild-type and the M184V reverse transcriptase variant of HIV-1 MT-4 cells.

FIG. 13. Relative infectivity of HIV-1 in HOS cells pretreated with C4'-ethynl-deoxy-2-fluoroadenosine. The relative infectivity is shown in comparison to the C4'-methyl-2-deoxyadenosine or C4'-ethyl-2-deoxyadenosine compounds.

FIG. 14. Efficacy and cellular cytotoxicity of C4'-Ethynl-2-deoxy-2-fluoro-adenosine in wild-type and M184V(RT) HIV-1.

FIG. 15. In vitro DNA extension using purified, recombinant HIV-1 RT, with varying amounts of C4'-methyl-2-deoxyadenosinetriphosphate and either (A) a DNA template or (B) and RNA template. Polymerase activity in the presence of dideoxyATP shows expected DNA products resulting from immediate chain terminators, while the dATP lane shows the fully extended DNA products. Bands in the lane containing equimolar amounts of ddATP and dATP correspond to pausing events at the site of incorporation of the nuclosidetriphosphate analog.

DETAILED DESCRIPTION

Compounds of the Invention

Figure 1:
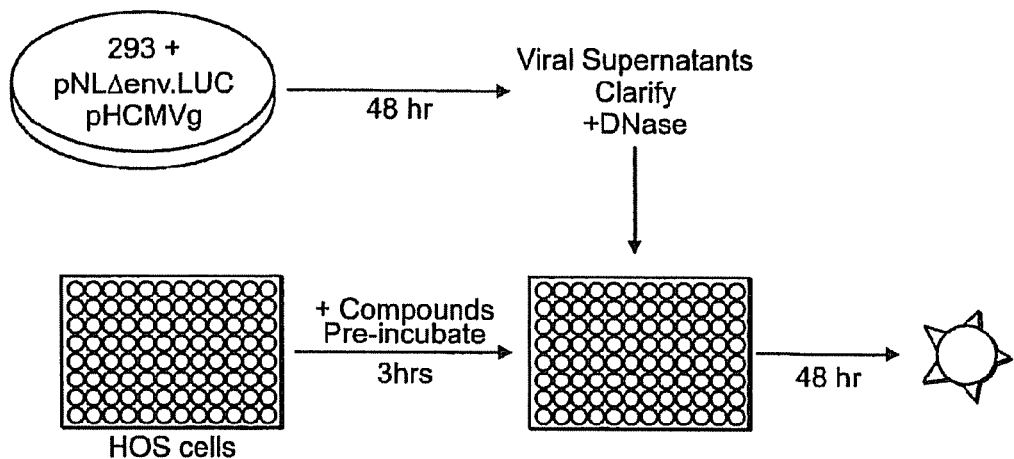
FIG. 1 provides a schematic of how compounds of formula I were screened against HIV-1 vectors. 293 cells were transfected with the plasmid carrying the viral genome, pNLNgo-MIVR-Δenv.LUC, that contains a deletion in the viral envelope coding region, and a luciferase reporter gene. Pseudotyping was carried out by co-transfecting with pHCMV-g,a plasmid which expresses the VSV-g envelope protein. Transfections were allowed to progress for 48 hours, at which point the viral supernatants were clarified of any cellular debris and applied to HOS cells which have been pre-incubated with compounds of formula I. After 48 hours, the cells were assayed for luciferase activity and the data was normalized to infections in the absence of compound of the invention.

In one aspect, the invention provides a compound of Formula (I), or pharmaceutically acceptable salt, solvate or hydrate thereof:

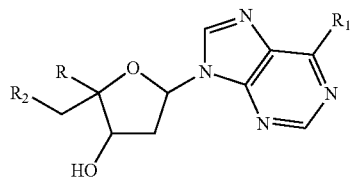

Formula (I)

wherein,

R is $C_2$-$C_{12}$alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;

$R^1$ is H, $C_1$-$C_{12}$alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2.

In one embodiment, the invention provides a compound of formula I wherein R is $C_2$-$C_{12}$ alkyl. In another embodiment, R is ethyl.

In certain embodiments, the invention provides a compound of formula I wherein $R_1$ is H or $NR_aR_b$. In a further embodiment, $R_1$ is $NH_2$.

In another embodiment, the invention provides a compound of formula I herein $R_2$ is OH.

In another aspect the invention provides for a pharmaceutical composition comprising one or more compounds of Formula (I) and a pharmaceutically acceptable carrier.

In one embodiment, the invention provides a pharmaceutical composition comprising one or more compounds of Formula (I), further comprising an additional therapeutic agent. In a further embodiment, the additional therapeutic agent is an antiviral agent.

In another aspect, the invention provides a kit comprising an effective amount of one or more compounds of Formula (I) in unit dosage form, together with instructions for administering the compound to a subject suffering from or susceptible to a viral infection.

Synthesis of Compounds of the Invention

The compounds of the invention were synthesized according to the steps found in reaction schemes 1-3. Scheme 1 shows the starting material 1, which was subjected to hydroxyl protection under basic conditions to provide protected alcohol 2 in high yields. Compound 2 was then deprotected under acidic conditions to afford compound 3. Compound 3 was converted to aldehyde 4, which was then reacted with formaldehyde under basic conditions to provide intermediate 5.

Scheme 1

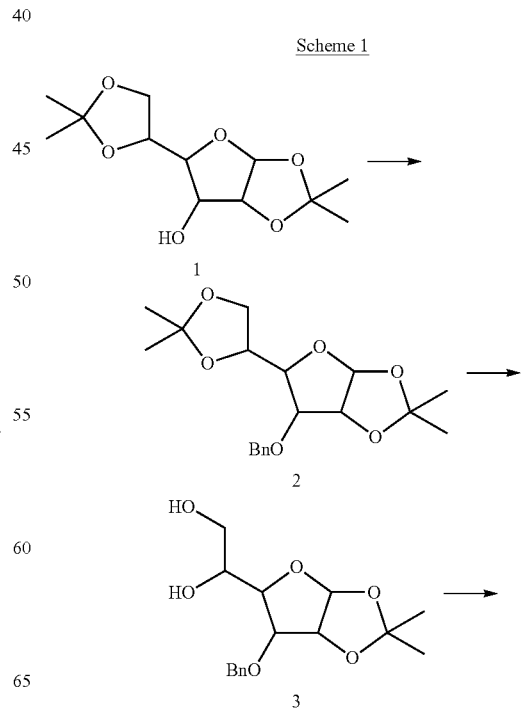

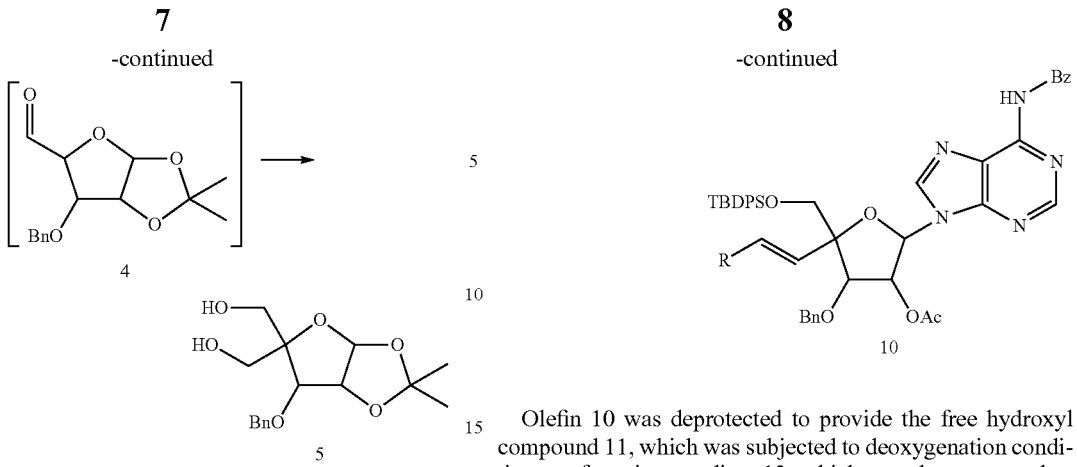

Intermediate 5 was hydroxyl protected with a silyl protecting group to afford 6, which underwent oxidation to provide aldehyde 7. Aldehyde 7 was subjected to a chain homologation/extension reaction, including but not limited to Wittig and Horner-Wadsworth chain elongation, to provide olefin 8. Deprotection of the acetonide group and treatment with acetic anhydride provided the diacetate 9, which was reacted with an adenine derivative to provide compounds of formula 10 (Scheme 2).

Olefin 10 was deprotected to provide the free hydroxyl compound 11, which was subjected to deoxygenation conditions to form intermediate 12, which was deoxygenated to compound 13. Further deprotection and olefin reduction provided compounds 14 and 15.

Scheme 2

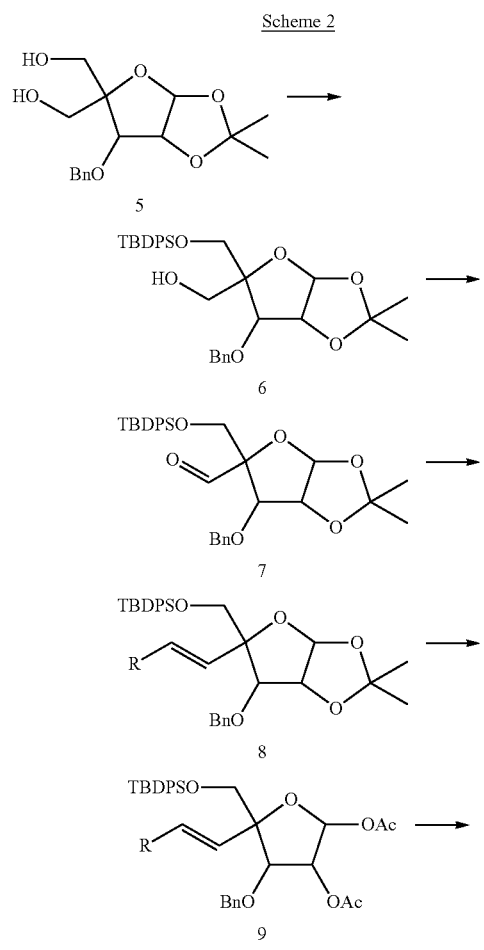

Scheme 3

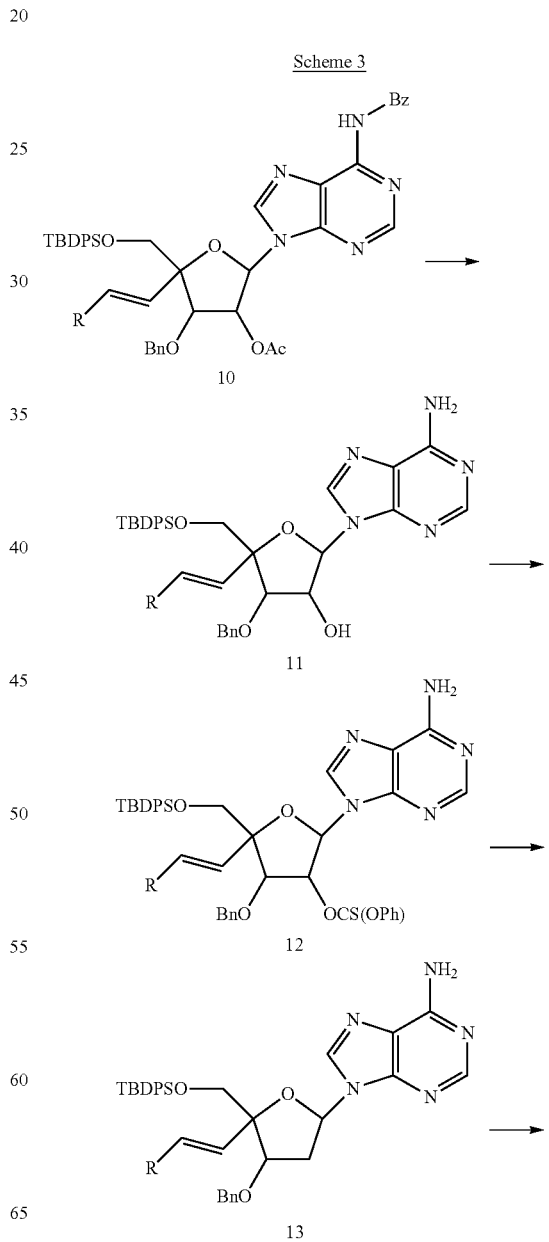

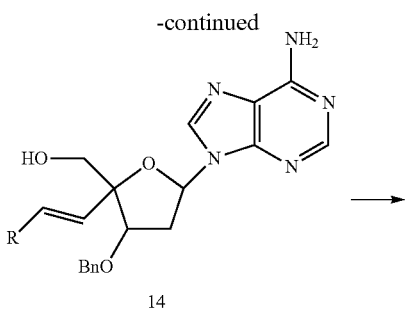

14

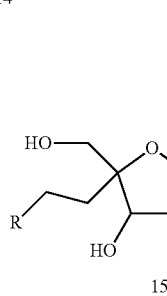

15

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treatment or prevention of disorders disclosed herein). The compounds produced by the methods herein can be incorporated into compositions, including solutions, capsules, crèmes, or ointments for administration to a subject (e.g., human, animal).

Methods of Treatment

In one aspect, the invention provides for a method of treating a subject suffering from or susceptible to a viral infection comprising administering to the subject an effective amount of one or more compounds of formula (I).

In one embodiment, the invention provides a method wherein the subject is infected with a retrovirus.

In another embodiment, the viral infection is HIV infection.

In another embodiment, the invention provides a method wherein the subject is identified as having a viral infection and the one or more compounds of formula (I) are administered to the identified subject.

In certain embodiments, the invention provides a method, further comprising administering an additional therapeutic agent.

In another aspect, the invention provides a method of treating a subject suffering from or susceptible to HIV infection comprising administering to the subject an effective amount of one or more compounds of formula (I).

In one embodiment, the HIV is wild type or drug resistant. In a further embodiment, the HIV is HIV-1.

In certain aspects, the invention provides a method of treating a subject suffering from or susceptible to HIV infection comprising administering to the subject an effective amount of one or more compounds of formula (I):

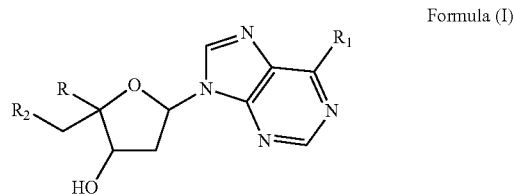

Formula (I)

wherein,

R is $C_1$-$C_{12}$ alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;

$R^1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the administered compound has a $CC_{50}$ of greater than 50 µM in a cytotoxicity assay comprising the following steps:

a) contacting cells with the compound of formula I; and b) determination of relative cytotoxicity using a detection kit;

wherein the detection kit comprises a luciferase reporter system and utilizes cellular ATP.

In certain embodiments, the cytotoxicity is measured to have a $CC_{50}$ of greater than 50 µM. In one embodiment, the cytotoxicity is measured to have a $CC_{50}$ of about 25 µM to about 100 mM. In another embodiment, the cytotoxicity is measured to have a $CC_{50}$ of about 50 µM to about 1000 µM. In another embodiment, the cytotoxicity is measured to have a $CC_{50}$ of about 50 µM to about 500 µM. In another embodiment, the cytotoxicity is measured to have a $CC_{50}$ of about 100 µM to about 250 µM.

In certain embodiments, the cells comprise cells that are infected with a viral infection, retroviral infection, HIV, or HIV-1.

In another aspect, the invention provides a method for identifying a compound of formula (I) which blocks viral infectivity,

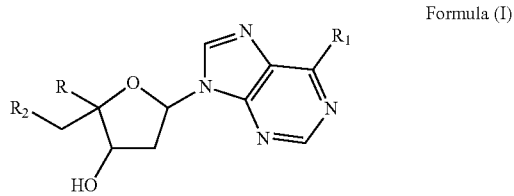

Formula (I)

wherein,

R is $C_1$-$C_{12}$ alkyl, $C_2$-$C_{12}$alkenyl, $C_3$-$C_{12}$alkynyl, $C_3$-$C_{12}$cycloalkyl, $C_3$-$C_{12}$aryl, $C_3$-$C_{12}$heteroaryl, $C_4$-$C_{12}$aralkyl, or $C_4$-$C_{12}$heteroaralkyl, each of which may be optionally substituted;

$R^1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the compound has a $CC_{50}$ of greater than 50 µM; the method comprising the following steps:

a) contacting cells with the compound of formula I;

b) detecting a decrease of viral infection; and c) determining an amount of decrease of viral infection.

In certain embodiments, the cells comprise cells that are infected with a viral infection, a retroviral infection, HIV or HIV-1.

Treatment of Diseases

The invention provides methods of treating or preventing a retroviral infection comprising the administration of a compound of formula I to a subject infected with or susceptible to infection by a retrovirus such as HIV.

Therapeutic methods of the invention can also include the step of identifying that the subject is in need of treatment of diseases or disorders described herein, e.g., identifying that the subject is in need of treatment for a viral infection. The identification can be in the judgment of a subject or a health professional and can be subjective (e.g., opinion) or objective (e.g., measurable by a test or a diagnostic method). Tests for retroviral infection such as HIV infection are known in the art and include polymerase chain reaction-based (PCR-based) amplification and detection of viral RNA; Western blot detection of anti-HIV antibodies; agglutination assays for anti-HIV antibodies; ELISA-based detection of HIV-specific antigens; and line immunoassay (LIA). In each of these methods, a sample of biological material, such as blood, plasma, semen, or saliva, is obtained from the subject to be tested. Thus, the methods of the invention can include the step of obtaining a sample of biological material (such as a bodily fluid) from a subject; testing the sample to determine the presence or absence of retroviral infection such as HIV infection, HIV particles, or HIV nucleic acids; and determining whether the subject is in need of treatment according to the invention.

The methods delineated herein can further include the step of assessing or identifying the effectiveness of the treatment or prevention regimen in the subject by assessing the presence, absence, increase, or decrease of a marker, including a marker or diagnostic measure of a retroviral infection such as HIV infection, HIV replication, viral load, or expression of an HIV infection marker; preferably this assessment is made relative to a measurement made prior to beginning the therapy. Such assessment methodologies are known in the art and can be performed by commercial diagnostic or medical organizations, laboratories, clinics, hospitals and the like. As described above, the methods can further include the step of taking a sample from the subject and analyzing that sample. The sample can be a sampling of cells, genetic material, tissue, or fluid (e.g., blood, plasma, sputum, etc.) sample. The methods can further include the step of reporting the results of such analyzing to the subject or other health care professional. The method can further include additional steps wherein (such that) the subject is treated for the indicated disease or disease symptom.

As discussed above, the invention includes methods for treating against a virus infection, including to treat mammalian cells that are infected with a retrovirus, particularly human cells that are infected with a retrovirus such as HIV.

Compounds of the invention may be administered singularly (i.e., sole therapeutic agent of a regime) to treat or prevent diseases and conditions such as viral infection as disclosed herein.

Compounds of the invention also may be administered as a "cocktail" formulation, i.e., coordinated administration of one or more compounds of the invention together with one or more other active therapeutics.

For an antiviral therapy, one or more compounds of the invention including those of Formula I may be administered in coordination with a regime of one or more other antiviral agents such as reverse transcriptase inhibitors such as dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxy-ethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (maraviroc, Pfizer). Because many of these drugs are directed to different targets, e.g., viral integration, a synergistic may result with this combination.

In one embodiment, one or more compounds of the invention including those of the formulae herein are used in conjunction with one or more therapeutic agents useful for treatment or prevention of HIV, a symptom associated with HIV infection, or other disease or disease symptom such as a secondary infection or unusual tumor such as herpes, cytomegalovirus, Kaposi's sarcoma and Epstein-Barr virus-related lymphomas among others, that can result in HIV immunocompromised subjects.

In certain embodiments of the invention, one or more compounds of the invention including those of Formula I are used in conjunction with a standard HIV antiviral treatment regimens. In another aspect, the treatment methods herein include administration of a so-called HIV-drug "cocktail" or combination therapy, wherein a combination of reverse transcriptase inhibitor(s) and HIV protease inhibitor(s) is co-administered.

For antiviral therapies, in a particular aspect, the compounds of the invention can be administered to HIV infected individuals or to individuals at high risk for HIV infection, for example, those having sexual relations with an HIV infected partner, intravenous drug users, etc.

Pharmaceutical Compositions

Pharmaceutical compositions and dosage forms of the invention comprise one or more of the active ingredients disclosed herein. Pharmaceutical compositions and dosage forms of the invention typically also comprise one or more pharmaceutically acceptable excipients or diluents.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

The invention also provides compositions comprising an effective amount of a composition containing a compound of the invention and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

Single unit dosage forms of the invention are suitable for oral, mucosal (e.g., nasal, sublingual, vaginal, buccal, or rectal), parenteral (e.g., subcutaneous, intravenous, bolus injection, intramuscular, intraarterial, intracutaneous, intraarticular, intrasynovial, intrasternal, intrathecal, intralesional and intracranial injection or infusion techniques.), by inhalation spray, topically, rectally, nasally, buccally, vaginally, via an implanted reservoir, or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A compound of this invention can also be administered in the form of suppositories for rectal administration.

Because of their ease of administration, tablets and capsules represent an advantageous oral dosage unit form, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the compounds of the invention. Examples of other carriers include colloidal silicon dioxide, magnesium stearate, cellulose, sodium lauryl sulfate, and D&C Yellow #10.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

A compound of the invention can, for example, be administered with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Definitions

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen," "halo," or "hal" means —F, —Cl, —Br or —I.

As used herein, the term "haloalkyl" means an alkyl group in which one or more (including all) of the hydrogen radicals are replaced by a halo group, wherein each halo group is independently selected from —F, —Cl, —Br, and —I.

The term "cycloalkyl" refers to a hydrocarbon 3-8 membered monocyclic or 7-14 membered bicyclic ring system having at least one saturated ring, or hydrocarbon 3-8 membered monocyclic or 7-14 membered bicyclic ring system having at least one non-aromatic ring, wherein the non-aromatic ring has some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, cyclodecyl, cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a $(C_1-C_6)$alkylene group. Aralkyl groups may be optionally substituted, either on the aryl portion of the aralkyl group or on the alkylene portion of the aralkyl group, with one or more substituents. Representative aralkyl groups include benzyl, 2-phenyl-ethyl, naphth-3-yl-methyl and the like.

The term "heteroaryl" refers to a 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P and Si, preferably O, N, and S, wherein the nonaromatic ring system is completely saturated. The term "heterocycloalkyl" also refers to nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Bicyclic and tricyclic ring systems may be fused ring systems or Spiro ring systems. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, 1,4-dioxa-8-aza-spiro[4.5]dec-8-yl, tetrahydrofuranyl, tetrahydrothienyl, thiirene, thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "hydroxyalkyl" or "hydroxylalkyl" refers to an alkyl substituent which is further substituted with one or more hydroxyl groups.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, or heterocycloalkyl group) is substituted or optionally substituted with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, alkylarylamino, cyano, nitro, mercapto, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cycloalkyl, heterocycloalkyl, wherein alkyl, alkenyl, alkyloxy, alkoxyalkyl, aryl, heteroaryl, cycloalkyl, are heterocycloalkyl are optionally substituted with alkyl, aryl, heteroaryl, halogen, hydroxyl, amino, mercapto, cyano, nitro, oxo (═O), thioxo (═S), imino (═NR), C(═N—NR$^k$)R$^k$, or C(═N—OR$^k$)R$^k$.

In other embodiments, substituents on any group (such as, for example, alkyl, alkenyl, alkynyl, aryl, aralkyl, heteroaryl, heteroaralkyl, cycloalkyl, and heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents for an alkyl, alkenyl, alkynyl, aryl, aralkyl, heteroaryl, heteroaralkyl, cycloalkyl, and heterocycloalkyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (═O), (═S), (═NR$^{15}$), C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocycloalkyl, or heteroaryl. Each R$^{16}$ is independently hydrogen, C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each R$^{17}$ is independently C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each C$_3$-C$_6$ cycloalkyl, aryl, heterocycloalkyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

The recitation of a listing of chemical groups in any definition of a variable herein includes definitions of that variable as any single group or combination of listed groups.

The compounds of this invention include the compounds themselves, as well as their salts, solvate, clathrate, hydrate, polymorph, or prodrugs, if applicable.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

The term "effective amount" is used throughout the specification to describe concentrations or amounts of compounds according to the present invention which may be used to produce a favorable change in the disease or condition treated, whether that change is a remission, a favorable physiological result, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

The term "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

In addition, some of the compounds of this invention may have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

EXAMPLES

The invention is further illustrated by the following examples which in no way should be construed as being further limiting. The compounds of the invention were synthesized according to the examples provided herein and according to any reaction schemes provided supra.

Example 1

Synthesis of Compounds of the Invention

6-Benzyloxy-5-(2,2-dimethyl-[1,3]dioxolan-4-yl)-2,2-dimethyl-tetrahydro-furo[2,3-d][1,3]dioxole

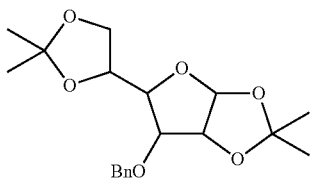

A flask was charged with 1,2,5,6-di-O-isoproylidene-α-D-allofuranose and DMF. To the reaction was added sodium hydride (NaH) and benzyl chloride (BnCl). The reaction was stirred, quenched, extracted, washed, dried, and the solvent was evaporated to provide the titled compound in 87% yield.

1-(6-Benzyloxy-2,2-dimethyl-tetrahydro-furo[2,3-d][1,3]dioxol-5-yl)-ethane-1,2-diol

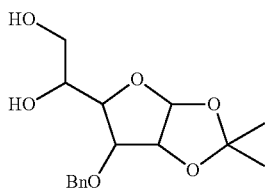 [SMILES: CC1(C)OC2OC(C(O)CO)C(OCc3ccccc3)C2O1]

To a flask charged with 6-Benzyloxy-5-(2,2-dimethyl-[1,3]dioxolan-4-yl)-2,2-dimethyl-tetrahydro-furo[2,3-d][1,3]dioxole was added 75% aqueous solution of acetic acid. The reaction was stirred, extracted, washed, dried and the solvent was evaporated to provide the titled compound in 80% yield.

(6-Benzyloxy-5-hydroxymethyl-2,2-dimethyl-tetrahydro-furo[2,3-d][1,3]dioxol-5-yl)-methanol

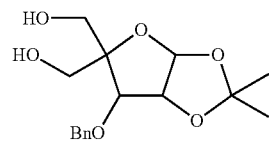 [SMILES: CC1(C)OC2OC(CO)(CO)C(OCc3ccccc3)C2O1]

A flask was charged with 1-(6-Benzyloxy-2,2-dimethyl-tetrahydro-furo[2,3-d][1,3]dioxol-5-yl)-ethane-1,2-diol, and to it was added NaIO$_4$ and water. There reaction was stirred, extracted, and concentrated. To the residue was added a 1:1 THF:H$_2$O solution, 37% aqueous formaldehyde, 1N NaOH, and the reaction was stirred. After completion, the reaction was extracted, washed, dried, and the solvent was evaporated to provide the titled compound in 98% over two steps.

[6-Benzyloxy-5-(tert-butyl-diphenyl-silanyloxymethyl)-2,2-dimethyl-tetrahydro-furo[2,3-d][1,3]dioxol-5-yl]-methanol

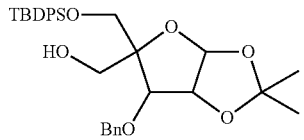

A flask was charged with (6-Benzyloxy-5-hydroxymethyl-2,2-dimethyl-tetrahydro-furo[2,3-d][1,3]dioxol-5-yl)-methanol, methylene chloride, triethyl amine, and TBDPS-Cl, and allowed to stir. The reaction was extracted, washed, and the solvent was evaporated to provide the titled compound in 61% yield.

23

6-Benzyloxy-5-(tert-butyl-diphenyl-silanyloxymethyl)-2,2-dimethyl-tetrahydro-furo[2,3-d][1,3]dioxole-5-carbaldehyde

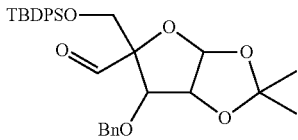

To a flask was added [6-Benzyloxy-5-(tert-butyl-diphenyl-silanyloxymethyl)-2,2-dimethyl-tetrahydro-furo[2,3-d][1,3]dioxol-5-yl]-methanol, methylene chloride, and Dess-Martin periodinane. The reaction was stirred, extracted, and the solvent was evaporated to provide the titled aldehyde in 96% yield.

(6-Benzyloxy-2,2-dimethyl-5-vinyl-tetrahydro-furo[2,3-d][1,3]dioxol-5-ylmethoxy)-tert-butyl-diphenyl-silane

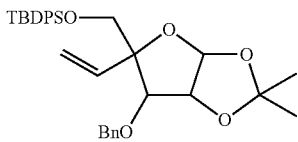

To a flask was added 6-Benzyloxy-5-(tert-butyl-diphenyl-silanyloxymethyl)-2,2-dimethyl-tetrahydro-furo[2,3-d][1,3]dioxole-5-carbaldehyde, THF, and n-BuLi. The reaction was stirred and a solution of $CH_3PPh_3Br$ in THF was added. The reaction was allowed to stir, was quenched, extracted, washed, and the solvent was evaporated to provide the titled product in 92% yield.

Acetic acid 3-acetoxy-4-benzyloxy-5-(tert-butyl-diphenyl-silanyloxymethyl)-5-vinyl-tetrahydro-furan-2-yl ester

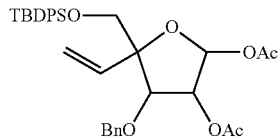

A flask was charged with (6-Benzyloxy-2,2-dimethyl-5-vinyl-tetrahydro-furo[2,3-d][1,3]dioxol-5-ylmethoxy)-tert-butyl-diphenyl-silane, Acetic acid, acetic acid anhydride, and $H_2SO_4$. The reaction was stirred, extracted, and the solvent was evaporated to provide the titled compound in 85% yield.

24

Acetic acid 2-(6-benzoylamino-purin-9-yl)-4-benzyloxy-5-(tert-butyl-diphenyl-silanyloxymethyl)-5-vinyl-tetrahydro-furan-3-yl ester

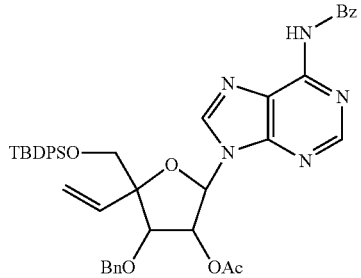

A flask was charged with Acetic acid 3-acetoxy-4-benzyloxy-5-(tert-butyl-diphenyl-silanyloxymethyl)-5-vinyl-tetrahydro-furan-2-yl ester, acetonitrile, the trimethylsilyl triflate (TMSOTf). To the reaction was added $N^6$-benzoyl adenine. The reaction was stirred, extracted, and the solvent was evaporated to provide the titled compound in 68% yield.

2-(6-Amino-purin-9-yl)-4-benzyloxy-5-(tert-butyl-diphenyl-silanyloxymethyl)-5-vinyl-tetrahydro-furan-3-ol

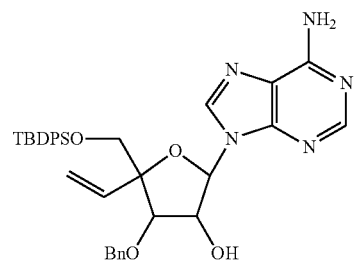

To a flask charged with Acetic acid 2-(6-benzoylamino-purin-9-yl)-4-benzyloxy-5-(tert-butyl-diphenyl-silanyloxymethyl)-5-vinyl-tetrahydro-furan-3-yl ester was added methanol and $NH_3$. The reaction was stirred, extracted, and the solvent was evaporated to provide the titled compound in 96% yield.

Thiocarbonic acid O-[2-(6-amino-purin-9-yl)-4-benzyloxy-5-(tert-butyl-diphenyl-silanyloxymethyl)-5-vinyl-tetrahydro-furan-3-yl]ester O-phenyl ester

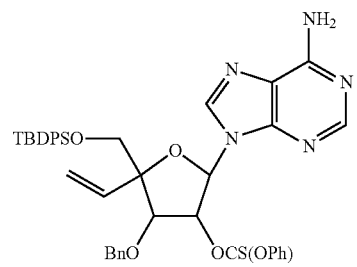

A flask was charged with 2-(6-Amino-purin-9-yl)-4-benzyloxy-5-(tert-butyl-diphenyl-silanyloxymethyl)-5-vinyl-tetrahydro-furan-3-ol, acetonitrile, dimethylamino pyridine (DMAP), and PhOCSCl. The reaction was stirred, extracted, and the solvent was evaporated to provide the titled compound in 82% yield.

9-[4-Benzyloxy-5-(tert-butyl-diphenyl-silanyloxymethyl)-5-vinyl-tetrahydro-furan-2-yl]-9H-purin-6-ylamine

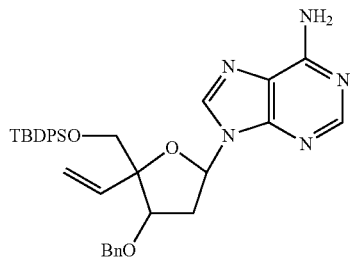

To a flask was added Thiocarbonic acid O-[2-(6-amino-purin-9-yl)-4-benzyloxy-5-(tert-butyl-diphenyl-silanyloxymethyl)-5-vinyl-tetrahydro-furan-3-yl]ester O-phenyl ester, toluene, tributyl tin hydride, and AIBN. The reaction was stirred at reflux, cooled back to room temperature, was extracted, and the solvent was removed to provide the titled compound in 90% yield.

[5-(6-Amino-purin-9-yl)-3-benzyloxy-2-vinyl-tetrahydro-furan-2-yl]-methanol

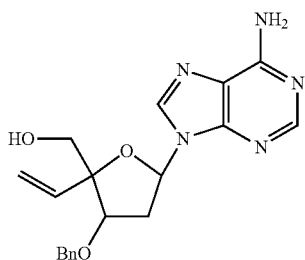 [SMILES: C=CC1(CO)OC(n2cnc3c(N)ncnc32)CC1OCc1ccccc1]

9-[4-Benzyloxy-5-(tert-butyl-diphenyl-silanyloxymethyl)-5-vinyl-tetrahydro-furan-2-yl]-9H-purin-6-ylamine, THF, and TBAF were added to a flask and allowed to stir. The reaction was extracted, and the solvent removed to provide the titled compound in 68% yield.

5-(6-Amino-purin-9-yl)-2-ethyl-2-hydroxymethyl-tetrahydro-furan-3-ol

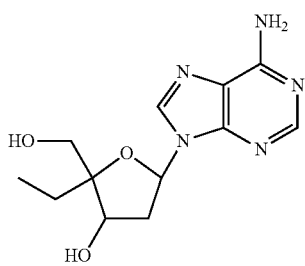 [SMILES: CCC1(CO)OC(n2cnc3c(N)ncnc32)CC1O]

[5-(6-Amino-purin-9-yl)-3-benzyloxy-2-vinyl-tetrahydro-furan-2-yl]-methanol was added to a flask. A 3.4% solution of HCOOH in methanol and Pd/C were added. The reaction was allowed to stir, was filtered and the solvent evaporated to provide the titled compound in 63% yield.

Example 2

Transfection, Infection, and Relative Infectivity Using Nucleoside Analogs Against HIV-1

Human embryonyl kidney cell culture line 293 was obtained from the American Type Culture Collection (ATCC). The human osteosarcoma cell line, HOS, was obtained from Dr. Richard Schwartz (Michigan State University, East Lansing, Mich.). Cell lines were maintained in Dulbecco's modified Eagles medium (Invitrogen, Carlsbad, Calif.), supplemented with 5% (v/v) fetal bovine serum, 5% newborn calf serum and penicillin (50 units/mL) plus streptomycin (50 μg/mL) (Quality Biological, Gaithersburg, Md.). VSV-g-pseudotyped HIV based vector was produced by transfection of 293 cells. On the day prior to transfection, 293 cells were transfected with 10 μg of PHCMV-g (obtained from Dr. Jane Burns, University of California, San Diego) using calcium phosphate precipitation. After 48 hours, virus-containing supernatants were harvested, clarified by low-speed centrifugation and filtration, and diluted 1-to-5 in preparation for infection assays. HOS cells were plated in 9 well luminescence cell culture plates at a density of 5000 cells in 100 μL per well the day prior to infection. On the day of infection, cells were pretreated with the compounds of the invention for 3 h. Infections were carried out by adding 100 μL of steadylite plus reagent (PerkinElmer, Waltham, Mass.) directly to the cells and measuring luminescence using a microplate reader. Activity was normalized to infections in the absence of target compounds for the appropriate NRTI variant. NFIT (University of Texas, Galveston, Tex.) was used to perform regression analysis on the data. $IC_{50}$ values or $EC_{50}$ values were determined from the fit model.

Figure 2:
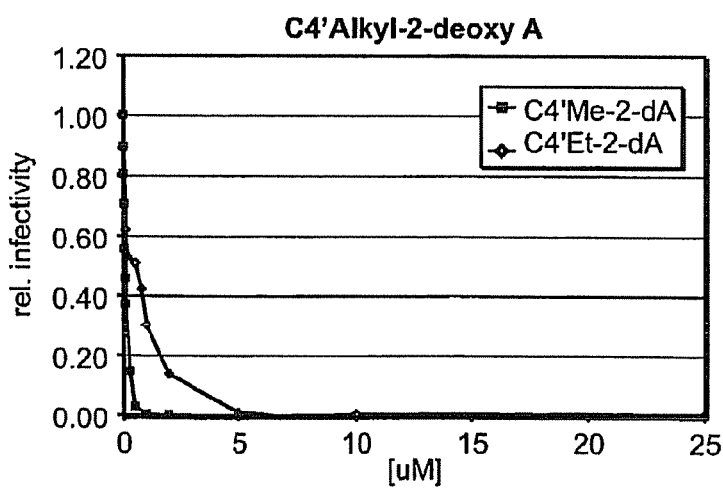
FIG. 2 shows the relative infectivity of HIV-1 vectors on HOS cells that have be pretreated with C4'Methyl-2-deoxy-adenosine (C4' Me-2-dA) or C4' Ethyl-2-deoxyadenosine (C4' Et-2-dA. In both cases, the target compounds are highly effective against HIV-1. Linear regression analysis was performed on the data to determine $EC_{50}$ values for each compound, which were determined to be 48 nM for the methyl compound, and 358 nM for the ethyl compound.

FIG. 2 shows the relative infectivity of HIV-1 vectors on HOS cells that have be pretreated with C4'Methyl-2-deoxyadenosine or C4' Ethyl-2-deoxyadenosine. In both cases, the target compounds are highly effective against HIV-1. Linear regression analysis was performed on the data to determine $EC_{50}$ values for each compound, which were determined to be 48 nM for the methyl compound, and 358 nM for the ethyl compound.

Figure 4:
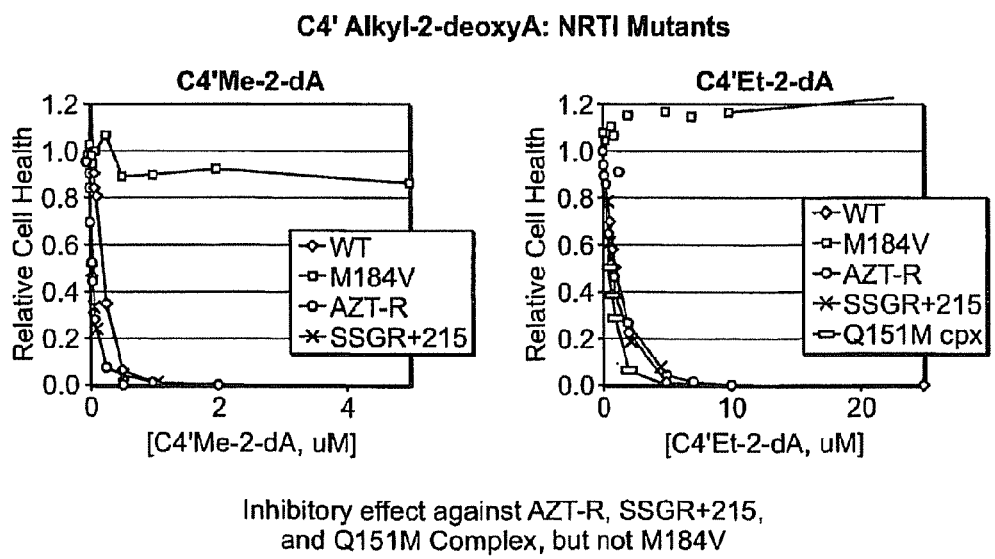
FIG. 4 shows that both C4'Me-2-dA ad C4'Et-2-dA were inhibitory against a few key NRTI resistance mutants; AZT-R, SSGR+215, and Q151M complex.

Compounds of the invention were next evaluated to examine the compounds against NRTI-resistant virus. In the vector based assays, it was demonstrated that both C4'Me-2-dA ad C4'Et-2-dA were inhibitory against a few key NRTI resistance mutants; AZT-R, SSGR+215, and Q151M complex (FIG. 4).

Example 3

Quantitative PCR

The effects of the target compounds on viral DNA production were determined by quantitative PCR. 293 cells were transfected as above and transfections were washed with PBS 8 hours post-transfection and fresh medium added. The transfection wash step was repeated 24 hours post-transfection and fresh medium was added. On the day prior to infection, HOS cells were plated at 2×10⁵ cells on to 60 mm plates. Virus-containing supernatants were harvested at 48 hours as above and treated with 20 U/mL of RNase-free DNase I (Roche Applied Science, Indianapolis, Ind.) and 30 U/mL of DNase Turbo (Ambion, Foster City, Calif.). Cells were pre-incubated with the target compounds for 3 h. For each target compound, the treated virus-containing supernatants were concentrated to 7.5 mL, and infections carried out by adding 1.75 mL each to 4 plates of HOS cells. Cells were harvested at 2, 4, 6, and 24 hour intervals and the viral DNA purified using the Qiagen EZ1 DNA tissue kit (Valencia, Calif.). Quantitative PCR (qPCR) was used to determine quantities of DNA corresponding to various steps along the viral DNA synthesis pathway. qPCR primers and probes used were as previously described. (Julias, J. G., Ferris, A. L., Boyer, P. L. and Hughes, S. H. (2001) *J. Virol.* 75, 6537-46.).

Figure 5:
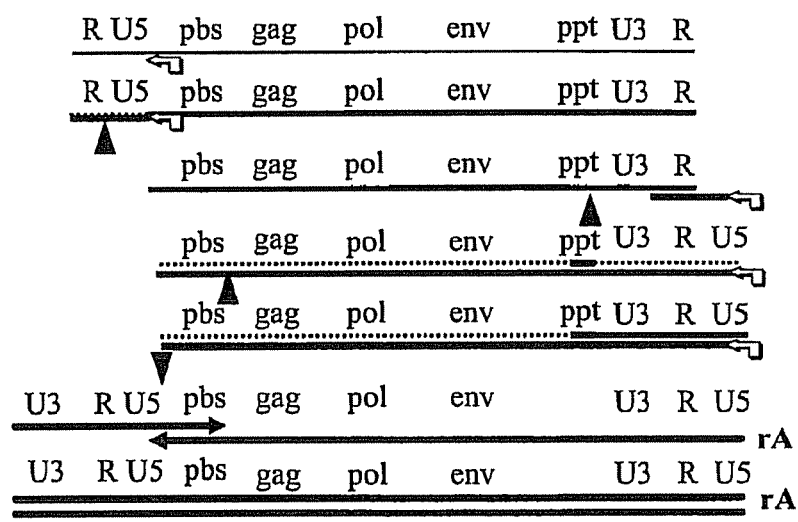
FIG. 5 is a schematic illustrating the steps of HIV-1 viral DNA synthesis. Viral DNA was isolated from infections over time and assayed by quantitative PCR to determine the amount of viral DNA produced corresponding to various points of DNA synthesis. The regions targeted by our PCR primers and probes are indicated and correspond to: initiation (RU5), minus strand transfer (U3), full length viral DNA (gag), and plus strand transfer (corresponding to second strand synthesis).

In order to determine that the compounds are targeting HIV-1 reverse transcriptase in the cell based assays, viral DNA was isolated from infections over time and assayed by quantitative PCR to determine the amount of viral DNA produced corresponding to various points of DNA synthesis (FIG. 5). The regions targeted by our PCR primers and probes correspond to: initiation (RU5), minus strand transfer (U3), full length viral DNA (gag), and plus strand transfer (corresponding to the initiation of second strand synthesis).

Figure 6:
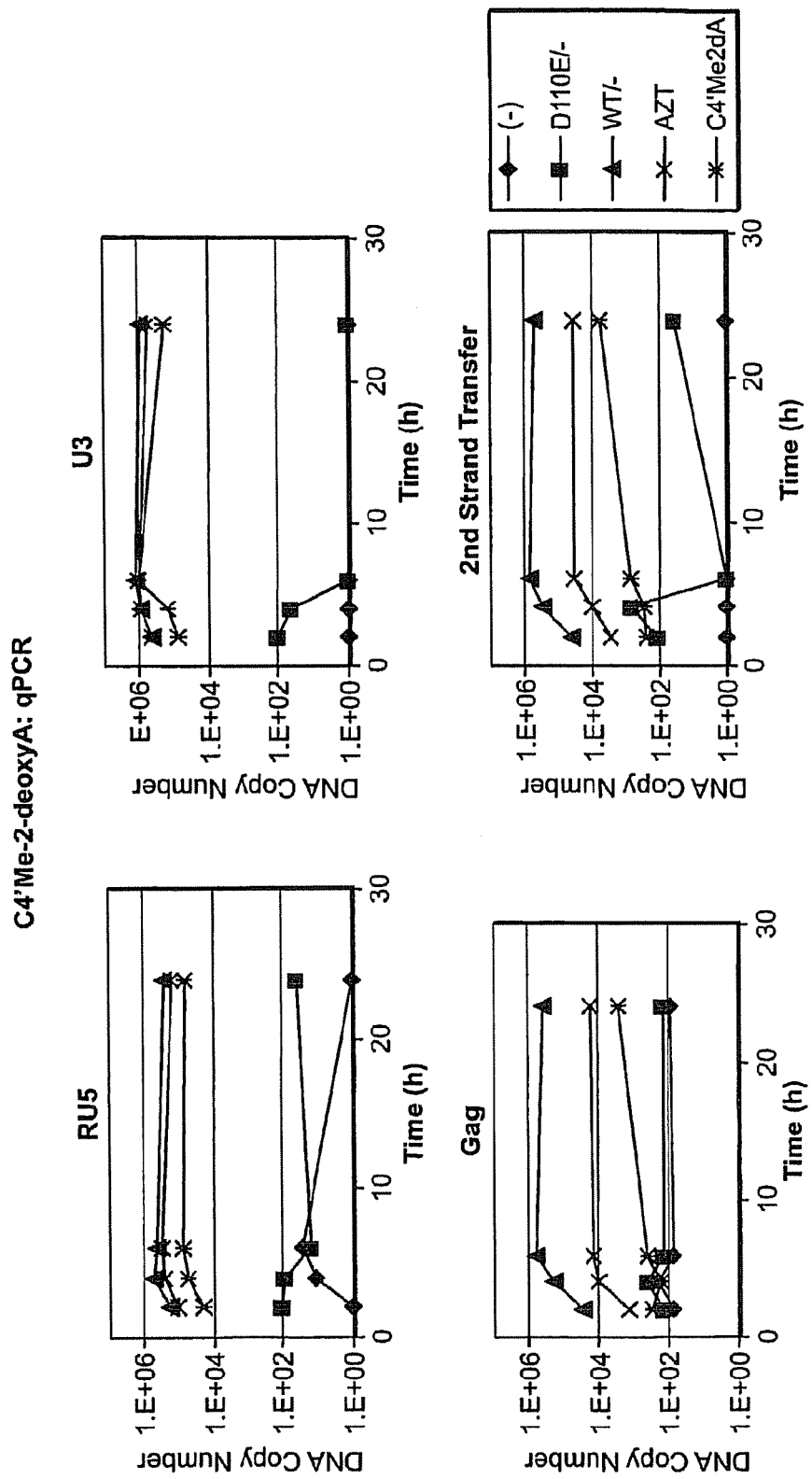
FIG. 6. Viral DNA was collected at 2, 4, 6 and 24 hours post-infection. As a control a D110E mutant was included as a RT negative control, as well as a wild-type infection carried out in the presence of AZT. The data indicate that late stage viral DNA synthesis (gag and $2^{nd}$ Strand Transfer) in the presence of C4' Me-2-dA is significantly diminished. C4' Me-2-dA inhibits DNA synthesis as well as or better than AZT.

Viral DNA was collected at 2, 4, 6 and 24 hours post-infection. As a control a D110E polymerase active site mutant was included as a RT negative control, as well as a wild-type infection carried out in the presence of AZT. The data indicate that late stage viral DNA synthesis (gag and 2$^{nd}$ Strand Transfer) in the presence of C4' Me-2-dA is significantly diminished. C4' Me-2-dA inhibits DNA synthesis as well as or better than AZT (FIG. 6).

Figure 7:
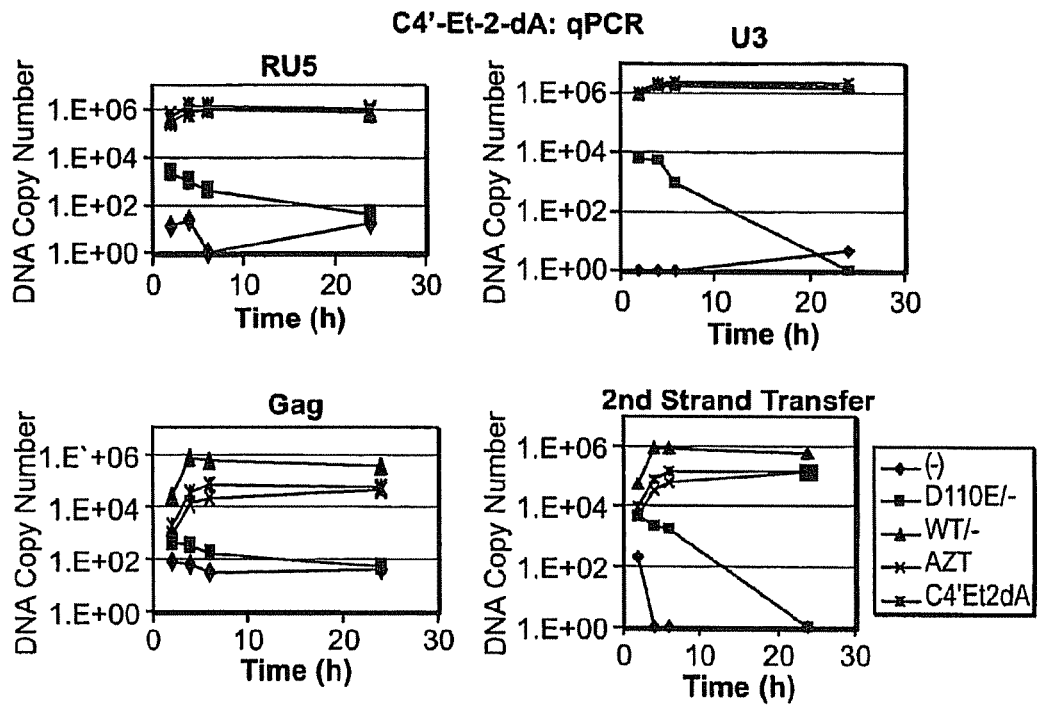
FIG. 7. Viral DNA was collected at 2, 4, 6 and 24 hours post-infection. As a control a D110E polymerase active site mutant was included as a RT negative control, as well as a wild-type infection carried out in the presence of AZT. The data indicate that late stage viral DNA synthesis (gag and $2^{nd}$ Strand Transfer) in the presence of C4' Et-2-dA is significantly diminished. C4' Et-2-dA inhibits DNA synthesis as well as or better than AZT.

Viral DNA was collected at 2, 4,6 and 24 hours post-infection. As a control a D110E mutant was included as a RT negative control, as well as a wild-type infection carried out in the presence of AZT. The data indicate that late stage viral DNA synthesis (gag and 2$^{nd}$ Strand Transfer) in the presence of C4' Et-2-dA is significantly diminished. C4' Et-2-dA inhibits DNA synthesis as well as or better than AZT (FIG. 7).

Example 4

Cellular Cytotoxicity

With any compound that would be used for drug therapy, cytotoxic effects need to be taken into consideration. In particular, the compounds of the invention are highly effective in the infectivity assay. Cytotoxic effects of the target compounds on HOS were determined by incubating cells with various concentrations of the appropriate target compounds over 48 hours. Cytotoxic effects were determined by measuring luciferase activity using the PerkinElmer ATPlite kit. Luciferase activity at each concentration was normalized to activity in the absence of any drug compounds.

Figure 3:
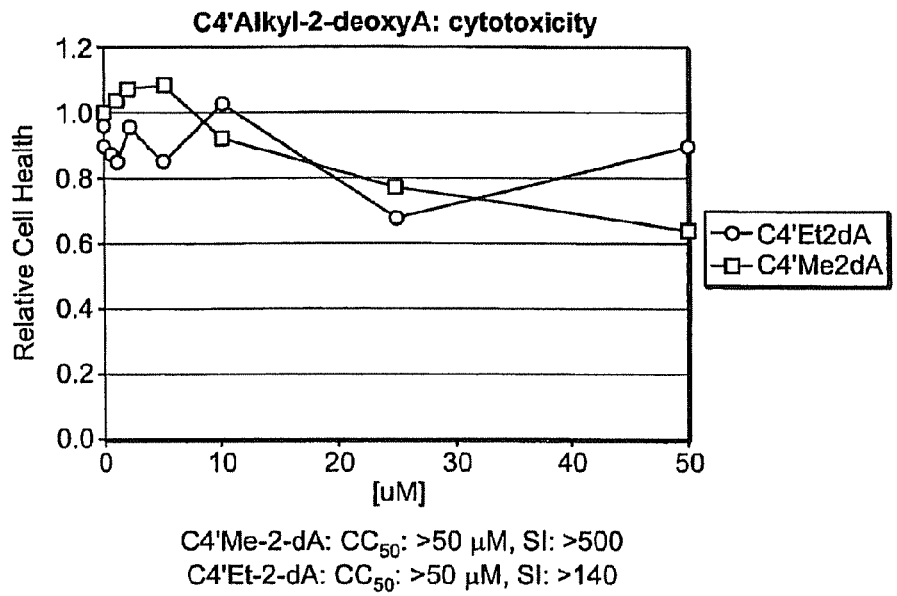
FIG. 3 indicates that the compounds of the invention were highly effective in the infectivity assay. To be sure cytotoxic effects were not being observed, the cells were incubated with only the compounds of the invention. Relative cytotoxicity was determined by using the PerkinElmer ATPlite detection kit, which contains a luciferase reporter system, and utilizes cellular ATP. The cellular ATP levels were used as a measure of relative cell health, with assumption that untreated cells will contain optimal ATP levels and thereby be the most healthy cells. Cells that exhibit cytotoxic effects from the target compounds will have decreased ATP levels as cytotoxicity increases.

FIG. 3 indicates that the compounds of the invention were highly effective in the infectivity assay. To monitor for cytotoxic effects, the cells were incubated with only the compounds of the invention. Relative cytotoxicity was determined by using the PerkinElmer ATPlite detection kit, which contains a luciferase reporter system, and utilizes cellular ATP. The cellular ATP levels were used as a measure of relative cell health, with assumption that untreated cells will contain optimal ATP levels and thereby be the most healthy cells. Cells that exhibit cytotoxic effects from the target compounds will have decreased ATP levels as cytotoxicity increases. FIG. 3 shows that the target compounds were not cytotoxic in the effective treatment range, with $CC_{50}$ values in excess of 50 μM. The $CC_{50}$ to $EC_{50}$ ratio was used in therapeutic development as the selectivity index. Higher SIs indicate that the compounds of the invention would not interfere with effective treatment owing to low cytotoxicity. The data shows that the SIs for the compounds of the invention is high, greater than 500 for C4'Me-2-dA and greater than 140 for C4'Et-2-dA. The data for C4'Me-2-dA is remarkable in contrast to work from Ohuri and others that indicated C4'Me-2-dA was cytotoxic in MT4 cell killing assays, yielding a low SI value.

Example 5

Materials and Methods

C4'-ethynl-deoxy-2-fluoroadenosine was obtained from Dr. Hiroaki Mitsuya (National Cancer Institute, HIV and AIDS Malignancy Branch). C4'-methyl-2-dexoyadenosinetriphosphate was prepared by Trilink Biotechnologies (San Diego, Calif.) from C4'-methyl-2-dexoyadenosine.

Cell-Based Assays.

Human embryonyl kidney cell culture line 293 was obtained from the American Type Culture Collection (ATCC). The human osteosarcoma cell line, HOS, was obtained from Dr. Richard Schwartz (Michigan State University, East Lansing, Mich.). The HeLa-derived TZM-bl cell culture line was obtained from the NIH AIDS Research & Reference Reagent Program. Cell lines were maintained in Dulbecco's modified Eagle's medium (Invitrogen, Carlsbad, Calif.) supplemented with 5% (v/v) fetal bovine serum, 5% newborn calf serum, and penicillin (50 units/mL) plus streptomycin (50 μg/mL) (Quality Biological, Gaithersburg, Md.). VSV-g-pseudotyped HIV was produced by transfection of 293 cells. On the day prior to transfection, 293 cells were plated in 100 mm dishes at a density of 9×10⁵ cells per plate. 293 cells were transfected with 10 μg of pNLNgoMIVR⁺ ΔEnv.LUC (wild-type or NRTI resistance mutant) and 3 μg of pHCMV-g (obtained from Dr. Jane Burns, University of California San Diego) using calcium phosphate precipitation. After 48 hours, virus-containing supernatants were harvested, clarified by low-speed centrifugation and filtration and diluted 1-to-5 in preparation for infection assays. HOS or TZM-bl cells were plated in 96 well luminescence cell culture plates at a density of 4000 cells in 100 μL per well the day prior to infection. On the day of infection, cells were pre-treated with the target compounds for 3 h. Infections were carried out by adding 100 μL of virus-containing supernatants to each well and incubating for 48 h. Infectivity was determined via a luciferase reporter assay. Luciferase activity was measured by adding 100 μL of steadylite plus reagent (PerkinElmer, Waltham, Mass.) directly to the cells and measuring luminescence using a microplate reader. Activity was normalized to infections in the absence of target compounds for the appropriate NRTI variant. Regression analysis on the data was performed using a 4-parameter sigmoidal binding model, $f(x)=a+b/(1+(x/c)^d)$ and $EC_{50}$ values were determined from the fit.

Cytotoxic effects were determined by treating HOS or TZM-bl cells with the target compounds and reading relative luciferase activity using the PerkinElmer ATPlite kit. Luminescence data was normalized to cell data in the absence of target compound. The data was fit as above and $IC_{50}$ values were determined from the fit.

Polymerase Extension Assay

The expression and purification of HIV-1 RT and the polymerase assays were done as previously described. For the extension assays, 7.0.mu.l of a 2.0.mu.l stock of synthetic DNA oligonucleotide (5'-GTCACTGTTCGAGCACCA-3' (SEQ ID NO:1); Biosource, CA) was 5' end-labeled, then annealed to an excess of either a DNA template (5'-AATCAGTGTAGACAATCCCTAGCTATGGTGCTCG AACA GTGAC-3' (SEQ ID NO:2)) or an RNA template (5'-AAUCAGUGUAGACAAUCCCUAGCUAUGGUGC UCGAA-CAGUGAC-3' (SEQ ID NO:3)). The A residue is the first nucleotide past the 3' end of the primer. The annealed template-primer (T/P) was suspended in a final concentration of 25.0 mM Tris (pH 8.0), 75 mM KCl, 8.0 mM $MgCl_2$, 100.0.mu.g/ml BSA, 10.0 mM CHAPS, and 10.0.mu.M each of dCTP, dGTP, and TTP. For the RNA template reactions, the mixture was also supplemented with 1 U/.mu.l of SuperAsin (Ambion). The reaction buffer was aliquoted to individual tubes, then supplemented with a total of 10.0.mu.M dATP and/or adenosine triphosphate analog (as described in the figure legend). The reactions were initiated by the addition of 1.0.mu.g RT and the reaction was incubated at 37.degree. C. for the various indicated time intervals. Reactions were stopped by the addition of EDTA and the reactions precipitated by the addition of isopropyl alcohol. The products were resuspended in formamide gel loading buffer II (Ambion), heated at 70.degree. for 5 min to denature the products, and fractionated on a 15% polyacrylamide sequencing gel.

Analog Inhibition Assay

The assay is similar to that described above. For the extension assays, the DNA oligonucleotide (5'-GTCACTGTTC-GAGCACCA-3 (SEQ ID NO:1)'; Biosource, CA) was 5' end-labeled, then annealed to an excess of a DNA template (5'-AATCAGTGTAGACAATCCCTAGCTATG-GTGCTCGAACAGTGAC-3' (SEQ ID NO:2)). The annealed template-primer (T/P) was suspended in a final concentration of 25.0 mM Tris (pH 8.0), 75 mM KCl, 8.0 mM $MgCl_2$, 100.0.mu.g/ml BSA, 10.0 mM CHAPS, 10.0.mu.M each of dCTP, dGTP, and TTP and 2.0 dATP. The reaction buffer was aliquoted to individual tubes, then supplemented with a range of analog concentrations (from 0.0 to 16.0.mu.M final). The reactions were initiated by the addition of 1.0.mu.g RT and the reaction was incubated at 37.degree. C. for 10 mins. Reactions were stopped by the addition of EDTA and the reactions precipitated by the addition of isopropyl alcohol. The products were resuspended in formamide gel loading buffer II (Ambion), heated at 70.degree. C. for 5 min to denature the products, and fractionated on a 15% polyacrylamide sequencing gel.

Results

Figure 8:
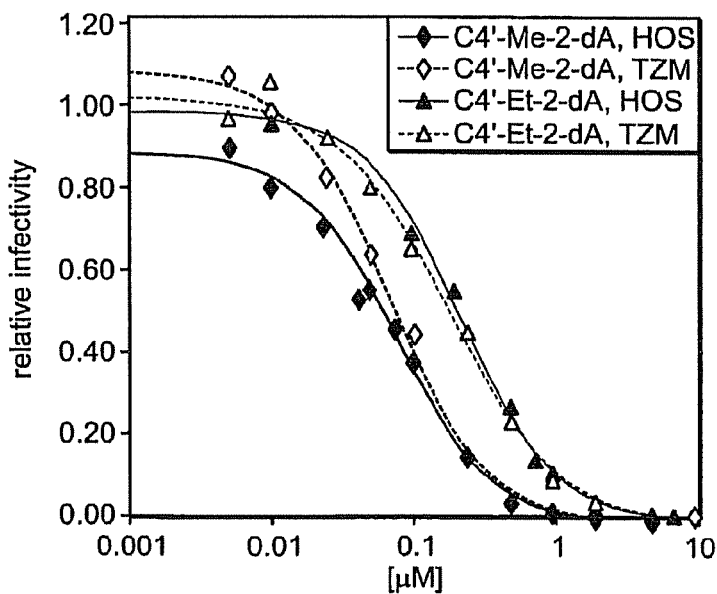
FIG. 8. Relative infectivity of HIV-1 in cells pretreated with either C4'-methyl-2-deoxyadenosine or C4'-ethyl-2-deoxyadenosine compounds.

In order to assess the viability of C4'-methyl- and -ethyl-2-deoxyadenosine as a drug candidate the compounds were tested in an alternate cell line. HeLa-derived TZM-bl cells were cultured and used in infectivity and cytotoxicity screens as previously described for HOS cells. The data indicated both compounds are equally as effective (FIG. 8), with similar selective indices (FIG. 9), in TZM-bl cells as in HOS cells.

The data indicated the compounds were effective against viruses carrying selected NRTI mutations, except for the M184V exclusion mutation. Further analysis of the data (FIG. 11) show the differences in anti-HIV-1 activity fall within one order of magnitude of wild-type. The largest difference in efficacy is seen with C4'-ethyl-2-deoxyadenosine and the AZT-R variant, with a 3.9 fold increase in the $EC_{50}$ value. Mitsuya and co-workers previously reported that C4'-ethynl-deoxy-2-fluoro-adenosine was an effective compound against NRTI-resistant HIV-1, including the M184V variant, in infected MT-4 cells (Ohrui 2006, Ohuri 2007, Kawamoto 2008). Unlike other compounds studied, this compound showed decreased cytotoxicity in MT-4 cells. The efficacy of this compound was compared against C4'-methyl- and -ethyl-2-deoxyadenosine in a single-cycle infectivity assay in HOS cells (FIG. 13). C4'-ethynl-deoxy-2-fluoro-adenosine has slightly improved efficacies against WT versus the compounds in this study, and shows significant improvement against the M184V variant, with a 2-fold increase in $EC_{50}$ values over wild-type.

Previous real-time PCR analysis of viral DNA indicated that there is no significant difference between treated and untreated infections at early events. However as DNA synthesis progresses in vivo, infections treated with C4'-alkylated-2-deoxyadenosine compounds produced diminished amounts of viral DNA relative to untreated infections, over time. In order to confirm the activity against HIV-1 RT, we performed DNA extension assays using purified, recombinant HIV-1 RT and C4'-methyl-2-dexoyadenosinetriphosphate (FIG. 15). The data show that incorporation of the triphosphate in RT polymerase assays results in pausing during DNA synthesis at the point of incorporation at short time points. At longer time points, extended DNA products are observed, indicating the compound does not act as a chain terminator. Polymerase reactions performed using mixtures of ATP and C4'-methyl-2-dexoyadenosinetriphosphate show pausing, as observed in the case of C4'-methyl-2-dexoyadenosinetriphosphate alone, and indicate the analog is able to compete with normal nucleosides during DNA synthesis.

INCORPORATION BY REFERENCE

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A compound of Formula (I), or pharmaceutically acceptable salt, solvate or hydrate thereof:

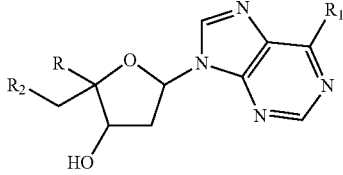

Formula (I)

wherein,
R is ethyl;
$R_1$ is H, $C_1$-$C_{12}$alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;
$R_2$ is $NR_aR_b$, $OR_b$, or $S(O)_nR_b$;
$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;
$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and
n is 0-2.

2. The compound of claim 1, wherein $R_1$ is H or $NR_aR_b$.
3. The compound of claim 2, wherein $R_1$ is $NH_2$.
4. The compound of claim 1, wherein $R_2$ is OH.

5. A pharmaceutical composition comprising one or more compounds of Formula (I) or pharmaceutically acceptable salt, solvate or hydrate thereof and a pharmaceutically acceptable carrier,

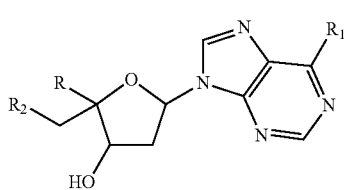

Formula (I)

wherein,
R is ethyl;
$R_1$ is H, $C_1$-$C_{12}$alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;
$R_2$ is $NR_aR_b$, $OR_b$, or $S(O)_nR_b$;
$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;
$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and
n is 0-2.

6. The composition of claim 5 further comprising an additional therapeutic agent.

7. The composition of claim 6 wherein the additional therapeutic agent is an antiviral agent.

8. A kit comprising an effective amount of one or more compounds of Formula (I) of claim 1 in unit dosage form, together with instructions for administering the compound to a subject suffering from a retroviral infection.

9. A method of treating a subject suffering from a retroviral infection comprising administering to the subject an effective amount of one or more compounds of formula (I) of claim 1.

10. The method of claim 9 wherein the retroviral infection is HIV infection.

11. The method of claim 9 wherein the subject is identified as having a retroviral infection and the one or more compounds of formula (I) are administered to the identified subject.

12. The method of claim 9 further comprising administering an additional therapeutic agent.

13. A method of treating a subject suffering from an HIV infection comprising administering to the subject an effective amount of one or more compounds of formula (I) of claim 1.

14. The method of claim 13, wherein the HIV is wild type or drug resistant.

15. The method of claim 14, wherein the HIV is HIV-1.

16. A method of treating a subject suffering from an HIV infection comprising administering to the subject an effective amount of one or more compounds of formula (I):

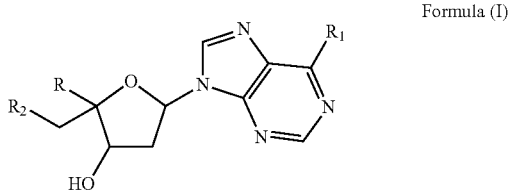

Formula (I)

wherein,

R is ethyl;

$R_1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the administered compound has a $CC_{50}$ of greater than 50 μM in a cytotoxicity assay comprising the following steps:

a) contacting cells with the compound of formula I; and b) determination of relative cytotoxicity using a detection kit;

wherein the detection kit comprises a luciferase reporter system and cellular ATP.

17. A method for identifying a compound of formula (I) which blocks viral infectivity,

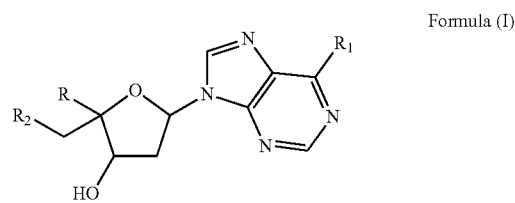

Formula (I)

wherein,

R is ethyl;

$R_1$ is H, $C_1$-$C_{12}$ alkyl, $C_3$-$C_{12}$aryl, $C_3$-$C_{12}$heteroaryl, $C_4$-$C_{12}$aralkyl, $C_4$-$C_{12}$heteroaralkyl, $NR_aR_b$, or $OR_b$, each of which is optionally substituted;

$R_2$ is $NR_aR_b$, $OR_b$, or $S(O)_nR_b$;

$R_a$, for each occurrence, is independently H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, or an optionally substituted $C_{3-12}$heteroaryl;

$R_b$, for each occurrence, is independently, H, an optionally substituted $C_{1-6}$alkyl, an optionally substituted $C_{4-12}$aralkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl, or $C_{1-6}$hydroxyalkyl; and n is 0-2;

or a pharmaceutically acceptable salt, solvate or hydrate thereof;

wherein the compound has a $CC_{50}$ of about greater than 50 μM;

the method comprising the following steps:

a) contacting cells with the compound of formula I;

b) detecting a decrease of viral infection; and c) determining an amount of decrease of viral infection.

* * * * *

SEQUENCE LISTING

<160> NUMBER OF SEQ ID NOS: 3

<210> SEQ ID NO 1
<211> LENGTH: 18
<212> TYPE: DNA

```
<213> ORGANISM: Artificial Sequence
<220> FEATURE:
<223> OTHER INFORMATION: Synthetic construct

<400> SEQUENCE: 1
gtcactgttc gagcacca                                              18

<210> SEQ ID NO 2
<211> LENGTH: 43
<212> TYPE: DNA
<213> ORGANISM: Artificial Sequence
<220> FEATURE:
<223> OTHER INFORMATION: synthetic construct

<400> SEQUENCE: 2
aatcagtgta gacaatccct agctatggtg ctcgaacagt gac                  43

<210> SEQ ID NO 3
<211> LENGTH: 43
<212> TYPE: RNA
<213> ORGANISM: Artificial Sequence
<220> FEATURE:
<223> OTHER INFORMATION: synthetic construct

<400> SEQUENCE: 3
aaucagugua gacaaucccu agcuauggug cucgaacagu gac                  43
```